United States Patent [19]
Miyoshi et al.

[11] Patent Number: 5,366,859
[45] Date of Patent: Nov. 22, 1994

[54] RADIOIMMUNOASSAY METHOD

[75] Inventors: Kinya Miyoshi; Masato Okada; Makoto Takada; Mayumi Goto, all of Ami, Japan

[73] Assignee: Mitsubishi Petrochemical Co., Ltd., Tokyo, Japan

[21] Appl. No.: 967,980

[22] Filed: Oct. 28, 1992

[30] Foreign Application Priority Data

Oct. 31, 1991 [JP] Japan .................. 3-311506

[51] Int. Cl.$^5$ .................. G01N 33/53; G01N 33/534; G01N 33/543
[52] U.S. Cl. .................. 435/5; 435/7.1; 435/7.22; 435/7.32; 435/7.5; 435/7.23; 436/504; 436/518; 436/526; 436/527; 436/817
[58] Field of Search ............... 436/504, 518, 526, 527, 436/531, 817; 435/5, 7.1, 7.22, 7.32, 7.5, 7.23

[56] References Cited

U.S. PATENT DOCUMENTS

| | | | |
|---|---|---|---|
| 4,034,074 | 7/1977 | Miles | 424/1 |
| 4,496,654 | 1/1985 | Katz et al. | 435/7.5 |
| 4,960,716 | 10/1990 | Harvey et al. | 436/542 |

FOREIGN PATENT DOCUMENTS

| | | |
|---|---|---|
| 0216191 | 4/1987 | European Pat. Off. . |
| 02042359 | 3/1990 | Japan . |
| 2190490 | 11/1987 | United Kingdom . |

OTHER PUBLICATIONS

Wisdom, Clin. Chem., vol. 22, No. 8, pp. 1243–1255 (1976).
Kim, B B, et al., J. Immunol. Methods, vol. 131, pp. 213–222 (1990).

*Primary Examiner*—Toni R. Scheiner
*Attorney, Agent, or Firm*—Oblon, Spivak, McClelland, Maier & Neustadt

[57] ABSTRACT

A radioimmunoassay which comprises the steps of reacting a first antibody (A) on an insoluble solid, which is specific for an antigen (B); an antigen (B); and a second antibody (C) derived from an animal different from that of the first antibody (A), which binds to the antigen (B) under conditions that the concentration of the second antibody (C) is higher than the dissociation constant between the second antibody (C) and the antigen (B) to obtain an immune complex (D); reacting the immune complex (D) with a radiolabeled probe (E) and then measuring the radioactivity of the solid precipitate or the reaction mixture, to measure the quantity of antigen (B). The method provides an assay with high sensitivity which does not depend on the sensitivity of the second antibody to be used.

19 Claims, 8 Drawing Sheets

RADIOIMMUNOASSAY METHOD

BACKGROUND OF THE INVENTION

1. Field of the Invention

This invention relates to a radioimmunoassay method.

2. Discussion of the Background

Conventional "sandwich" immunoassays generally employ the reaction between an antigen and a first antibody immobilized on an insoluble solid, then a second antibody labeled with a radioisotope or enzyme is reacted with the immuno complex, and finally the radioactivity or enzymatic activity is measured. Among sandwich assays which use a second antibody labeled with an enzyme, there is no limit to the amount of labeled second antibody that can be used, so that even when the second antibody does not have high sensitivity (i.e., the dissociation constant between antibody and antigen is large) the overall sensitivity of the assay can be enhanced by using the second antibody in high concentration. However, enzyme activity is harder to detect than the specific activity of radioisotopes, so that extremely high sensitivity cannot generally be obtained with enzymatic systems. Thus, there has been employed an improved method in which many labeled enzymes are bound per one molecule of the "second antibody" used to bind to an antigen, e.g. the avidin biotin complex method (Practice and Theory of Enzyme Immunoassays, P. Tijssen, Elsevier, 1985). However, even when these methods are used, measurement sensitivity in enzyme immunoassays cannot equal the sensitivity of a radioactive label, and it is difficult to obtain a measurement system with high sensitivity (see Japanese Provisional Patent Publication No. 118656/1988).

On the other hand, radioimmunoassays using a second antibody labeled with a radioisotope provide high measurement sensitivity since radioactivity can be detected at a lower concentration as compared with enzymic activity. However, the amount of radioactivity that can be added to a measurement system is limited, so that the concentration of the second antibody is limited to relatively low values. Furthermore, when the only available second antibody has inherently low sensitivity, the second antibody does not bind sufficiently to the antigen, therefore the overall sensitivity of the measurement system cannot be improved sufficiently by merely raising the concentration of the second antibody.

To describe the situation more specifically, the ratio of antigen bound to a second antibody relative to the amount of antigen not bound to a second antibody ([AgAb2]/[Ag]) in a reaction mixture is determined by the concentration of the second antibody [Ab2] and a dissociation constant between the second antibody and the antigen (Kd) as shown in the following formula.

$$\frac{[AgAb2]}{[Ag]} = \frac{[Ab2]}{Kd}$$

That is, the higher the concentration of second antibody and the smaller the dissociation constant, the larger the amount of second antibody that is bound to the antigen, whereby measurement sensitivity is heightened.

However, the dose of radioactivity which can be used in a measurement system is limited, so that the concentration of the second antibody is limited. When the dissociation constant of the second antibody is large, a measurement system having sufficient sensitivity cannot be obtained (Kodo Obata et al., The Japanese Journal of "Nuclear Medicine", Vol. 26, No. 3 (1989)).

As described above, it has conventionally been considered very important to obtain a second antibody with high sensitivity in order to obtain an immunoassay system with high sensitivity. However, it is often difficult to obtain an antibody with sufficiently high sensitivity, and great efforts have been made therefor.

Further, in conventional techniques, the second antibody is labeled directly. Thus, when two or more measurement systems are to be prepared in order to measure two or more antigens, then two or more secondary antibodies which identify the respective antigens must be labeled separately. This requirement results in an increase in cost.

SUMMARY OF THE INVENTION

The present invention has been made in order to provide a radioimmunoassay based on an entirely novel concept in which a high concentration of the second antibody can be used irrespective of the amount of radioactivity. The method provides an immunoassay with high sensitivity even when the second antibody has low sensitivity.

The present invention is a radioimmunoassay which comprises the steps of:

(i) reacting a first antibody (A) that is specific for an antigen (B) and bound to an insoluble solid, with an antigen (B) and a second antibody (C) derived from an animal species that is different from the first antibody (A), under conditions such that the concentration of the second antibody (C) is higher than the dissociation constant between the second antibody (C) and the antigen (B), to obtain an immune complex (D), (ii) reacting the immune complex (D) and a radiolabeled probe (E) which specifically reacts with the second antibody (C), and then (iii) measuring the radioactivity of the insoluble solid or the reaction mixture obtained in the above step (ii) to determine an amount of the above antigen (B).

DETAILED DESCRIPTION OF THE PREFERRED EMBODIMENTS

The antigen (B) in the present invention may be any substance that has antigenicity, for example, polypeptides comprising 3 or more amino acids, steroid nuclei and derivatives thereof. Suitable peptide hormones include parathyroid hormone related protein (PTHrP), parathyroid hormone (PTH), calcitonin, adrenocorticotropic hormone (ACTH), adrenocorticotropic hormone releasing factor, thyrotropic hormone, thyrotropic hormone releasing factor, insulin, growth hormone, human chorionic gonadotropin $\beta$ sub-unit, luteinizing hormone, follicle-stimulating hormone, arginine vasopressin (AVP), atrial natriuretic peptide (ANP), brain natriuretic peptide (BNP) and endothelin (ET). Steroid hormones include cortisol, estradiol, androsterone, androstenedione and vitamin D. Other suitable antigens are thyroxine, triiodothyronine, serum proteins (e.g. IgG, IgA, IgM, IgE, IgD, bone Gla protein, $\alpha$-fetoprotein and $\beta$-2-microglobulin), carcinoma-related antigens (a carcinoembryonic antigen (CEA), ferritin, POA, CA19-9 and CA125), or antigenic components of bacteria, viruses and protozoans relating to various diseases (e.g. streptococcus, hepatitis virus, herpes virus, Toxoplasma gondii and Plasmodium). Among them, when the concentration in a sample (e.g. blood) is so low that an assay with very high sensitivity is required, and, as in the sandwich-type assay, the antigen requires an antibody with high sensitivity to one site or all sites of two or more antigen-determining sites on the molecule, then the assay according to the present invention is particularly effective. Examples of such antigens include parathyroid hormone-related protein (PTHrP), atrial natriuretic peptide (ANP), endothelin (ET) and adrenocorticotropic hormone (ACTH). Among them, PTHrP is particularly preferred as the antigen (B) since its concentration in blood is low and it is difficult to obtain an antibody to it with high enough sensitivity for a conventional assay.

As the first antibody (A), there may be mentioned polyclonal antibodies obtained by inoculating the antigen to a vertebrate such as rabbit, goat, sheep and guinea pig according to conventional methods or monoclonal antibodies obtained from a hybridoma cells derived from cell fusion between cells which produce the required antibody and a myeloma cell line according to the method described in Köhler, G. and Milstein, C., Nature 256, 495 (1975). The preferred fusion partners are derived from mouse. The myeloma cells are preferably derived from the same species and the same strain as the antibody-producing cells. These antibodies are used after purification by ammonium sulfate fractionation, DEAE cellulose chromatography or affinity chromatography before use (Antibodies A Laboratory Manual by Ed Harlow and David Lane (Cold Spring Harbor Laboratory pp. 283 (1988)). The insoluble solid may be an inorganic carrier such as glass (e.g. porous glass and frosted glass), a silicic carrier such as silica gel and bentonite, or a magnetic material. Suitable organic carriers include plastics, polymer gel (e.g. polysaccharides such as dextran and agarose or polyacrylamide gel) and filters. Among these glass (e.g. glass beads and glass test tubes) and plastics (e.g. plastic beads, plastic tubes and plastic trays) are preferred since an antibody can be bound simply, easily and stably and their handling is easy.

Methods of binding the first antibody to the insoluble solid include a method of chemically binding glass to an antibody, for example, a method of using a silane coupling agent and, if necessary, a crosslinking agent (Japanese Provisional Patent Publication No. 108696/1979); a method of physical adsorption (U.S. Pat. Nos. 4,280,992 and 3,682,761); a method of physically adsorbing an antibody to plastic (Antibodies A Laboratory Manual by Ed Harlow and David Lane (Cold Spring Harbor Laboratory, p. 605, (1988)); or a method of reacting avidin immobilized on a solid with biotin chemically bound to an antibody to effect immobilization efficiently.

As the second antibody (C), there may be mentioned polyclonal antibodies derived from an animal species which identify the antigen (B) and are different from the first antibody. For example, when the first antibody is derived from rabbit, the second antibody can be derived from goat, sheep, guinea pig or the like; and when the first antibody is derived from sheep, the second is an antibody derived from rabbit, goat, guinea pig or the like. If the first antibody is a monoclonal antibody, a polyclonal antibody specific for the same antigen may be used as the second antibody. The second antibody may include antiserum, a hybridoma culture solution, ascites and immunoglobulins obtained by purifying them. When avidin or streptavidin is used as a probe, the second antibody is purified by known methods and then biotin is chemically bound thereto.

According to the assay of the present invention, measurement sensitivity can be effectively improved as compared with conventional methods particularly when the sensitivity of the second antibody is low, namely when the dissociation constant between the second antibody and the antigen is large. When the dissociation constant between the second antibody and the antigen is $10^{-6}$ to $9 \times 10^{-12}$ mol/l, preferably $10^{-8}$ to $10^{-11}$ mol/l, measurement sensitivity can be particularly improved as compared with the conventional method. However, the dissociation constant is not limited to the above value and may vary depending on the concentration of the antigen to be measured.

The concentration of the second antibody (concentration as immunoglobulin) is mainly determined by the dissociation constant (Kd) of the reaction between the second antibody and the antigen, and it is desirably 0.1 Kd to 100 Kd, preferably 1 Kd to 10 Kd. For example, when Kd is $10^{-9}$ mol/l, the concentration of the second antibody should be $1 \times 10^{-10}$ to $1 \times 10^{-7}$ mol/l, preferably $1 \times 10^{-9}$ to $1 \times 10^{-8}$ mol/l. However, the concentration is not limited to the above range and may vary depending on the concentration of the antigen in a sample to be tested and the labeling ratio or concentration of the radiolabeled probe (E).

Here, the dissociation constant can be easily measured by a general method (e.g. the Scatchard plot analysis method described in P. Tijssen, "Practice And Theory Of Enzyme Immunoassays" (1985) Elsevier Science Publishers). That is, the dissociation constant (Kd) is determined by the concentration of a complex [AbAg] between an antibody and an antigen, the concentration of the antigen [Ag] which is not bound to the antibody, and the concentration of the antibody [Ab] which is free from the antigen, as shown in the following formula.

$$Kd = \frac{[Ag][Ab]}{[AbAg]}$$

Here, when [Ag] is represented by F, [AbAg] is represented by B, and the total concentration of antibody in the reaction mixture is represented by $[Ab]_{TOTAL}$, then $[Ab]=[AB]_{TOTAL}-B$ and the above formula can be changed as shown below.

$$\frac{B}{F} = \frac{1}{Kd}([Ab]_{TOTAL} - B)$$

In the above formula, the bound/total ratio (B/T) of an antigen which is bound to an antibody to the total antigen and B/F ratio can be measured by a tracer experiment. Further, B can be calculated from the amount of total antigen added to the reaction mixture and B/T. B and B/F can be measured by changing the amount of antigen added to the reaction mixture variously. When the results are plotted on a graph with B as the abscissa and B/F as the ordinate, a reciprocal of the slope of its approximate line is the dissociation constant.

The immune complex (D) can be obtained by reacting the first antibody (A), the antigen (B) and the second antibody (C) at the above concentrations simultaneously or successively. For example, the immune complex can be obtained by incubating a mixture of buffer solution containing an insoluble solid to which the first antibody is bound, or an insoluble solid on which avidin is immobilized and the first antibody is biotinylated, a sample to be tested containing the antigen, and a second antibody-containing buffer solution simultaneously or successively. After incubation, the reaction mixture is removed from the insoluble solid. Subsequently, a washing solution such as distilled water, saline, a phosphate buffered solution or a dilute solution of surfactant is added, and then an operation of washing the insoluble solid is repeated several times (e.g. once to three times) to isolate the immune complex from any unreacted product.

The radiolabeled probe (E) can be obtained by labeling a probe that reacts specifically with the second antibody. As such a probe, there may be mentioned an antibody which identifies immunoglobulin derived from the same species of animal as that of the second antibody, e.g., when the second antibody is derived from rabbit—an anti-rabbit immunoglobulin-goat antibody. Further, when biotin is bound to the second antibody, avidin or streptavidin can be used as the probe. The probe is labelled by using a radioisotope, e.g. $^{125}I$, $^{131}I$, $^{3}H$ and $^{14}C$, preferably $^{125}I$ which has a long half-life and high specific activity and thus can be measured easily. Methods of labeling compounds with radioisotopes are described in W. H. Hunter and F. C. Greenwood, Nature 194, 495 (1962).

The immune complex (D) and the radiolabeled probe (E) react while incubating the immune complex and a buffer solution containing the labeled probe. Incubation can be carried out under ordinary conditions, e.g. at 2° to 50° C., preferably 20° to 30° C., for 5 minutes to 2 days, preferably 5 hours to one day. After incubation, the reaction product of the immune complex and the radiolabeled probe is washed with a washing solution and the radioactivity is measured by a well-type scintillation gamma counter (e.g. ARC-1000, trade name, manufactured by Aloka Co.).

The concentration of the antigen in a test sample can be measured by comparing the observed radioactivity of the sample and the radioactivity of a calibration curve prepared with an antigen of known concentration.

EXAMPLES

In the following, the present invention is described in detail by referring to Examples and Comparative examples, which are not intended to be limiting.

Example 1

Measurement of parathyroid hormone-related protein (PTHrP)

(a) Preparation of PTHrP standard solution

According to the method described in Biorn Nilsson, Lars Abrahamsen, "Method in Enzymology", 185 (1990) 144, PTHrP genes (cDNA) (Arthur E. Broadus et al., Proceedings of National Academy of Science, USA, 85 597 (1988)) obtained from Yale University in the U.S.A. were integrated in a protein A-fused protein-emerging vector pRIT2T (trade name, produced by Farmacia Co.), and introduced into *Escherichia coli* (N4830-1 strain, produced by Farmacia Co.). After the *Escherichia coli* was grown, a fused protein of PTHrP and protein A was produced, the fused protein was extracted, and PTHrP and protein A were chemically cleaved by treatment with BrCN to obtain crude PTHrP. The crude PTHrP was purified by affinity chromatography, ion exchange chromatography and gel filtration. After the resulting PTHrP was hydrolyzed, the concentration was quantitated by an amino acid analysis method, and then the PTHrP was prepared so as to have a concentration of 0.32 to 1,000 pmol/l by using a phosphate buffered saline containing 5% bovine serum albumin, 0.8% bovine γ-globulin and 0.05% polyoxyethylene(20)sorbitan monolaurate.

(b) Preparation of anti-PTHrP monoclonal antibody (first antibody)-binding plastic beads From spleen cells obtained from mice (Balb/c) immunized with PTHrP (1-34) (produced by Peninsula Co.) conjugated thyroglobulin and mouse myeloma cells, a monoclonal hybridoma was obtained according to the method described in "Monoclonal Antibody Experiment Manual" (1987) edited by Sakuji Tomiyama and Tamie Ando published by Kodansha. Subsequently, the resulting monoclonal hybridoma was transplanted into mice, and the obtained ascites were purified to prepare anti-PTHrP monoclonal immunoglobulin. The anti-PTHrP monoclonal immunoglobulin prepared was coated on plastic beads according to the method described in the above literature "Practice and Theory of Enzyme Immunoassays".

(c) Preparation of anti-PTHrP polyclonal antibody (second antibody)

After PTHrP (50-83) synthesized by an automatic solid phase peptide synthesizer manufactured by Applied Biosystems Co. was bound to thyroglobulin, rabbits were immunized therewith to obtain anti-PTHrP antiserum. Said antiserum was purified by affinity chromatography to obtain an anti-PTHrP polyclonal antibody having high specificity. The resulting antibody was used as the second antibody.

(d) Measurement of dissociation constant between anti-PTHrP polyclonal antibody (second antibody) and PTHrP (1-87) (antigen)

(i) Preparation of $^{125}I$-PTHrP (1-87)

The above PTHrP (1-87) was labeled with $^{125}$I in accordance with the method described in J. I. Thorell and B. G. Johansson, Biochem. Biophs. Acta 251, 263 (1971) purified by reverse phase high performance liquid chromatography, and then prepared so as to have a concentration of 400 Bq/0.1 ml by using a phosphate buffered saline containing 2% bovine serum albumin.

(ii) Preparation of B/F separating agent

A phosphate buffered saline containing anti-rabbit immunoglobulin-goat serum (diluted 256 fold) (produced by Immunobiological Laboratories, Japan), normal rabbit serum (diluted 1024 fold) (produced by Immunobiological Laboratories, Japan) and 12.5% of polyethylene glycol was prepared and used as a B/F separating agent.

(iii) Measurement of dissociation constant

To 0.1 ml of a solution of the above second antibody (anti-PTHrP polyclonal immunoglobulin) were added 0.1 ml of the standard PTHrP solution and 0.1 ml of the $^{125}$I-PTHrP (1-87) solution, and the mixture was incubated at 4° C. for 48 hours. Then, 0.5 ml of the B/F separating agent was added thereto, and the supernatant was removed by centrifugation. The radioactivity of the precipitate was measured by a well-shaped scintillation gamma counter ARC-1000 (trade name, manufactured by Aloka Co.). According to the method described in the above literature "Practice And Theory Of Enzyme Immunoassays", Scatchard analysis was carried out to determine a binding constant. Its reciprocal was designated a dissociation constant.

Figure 1:
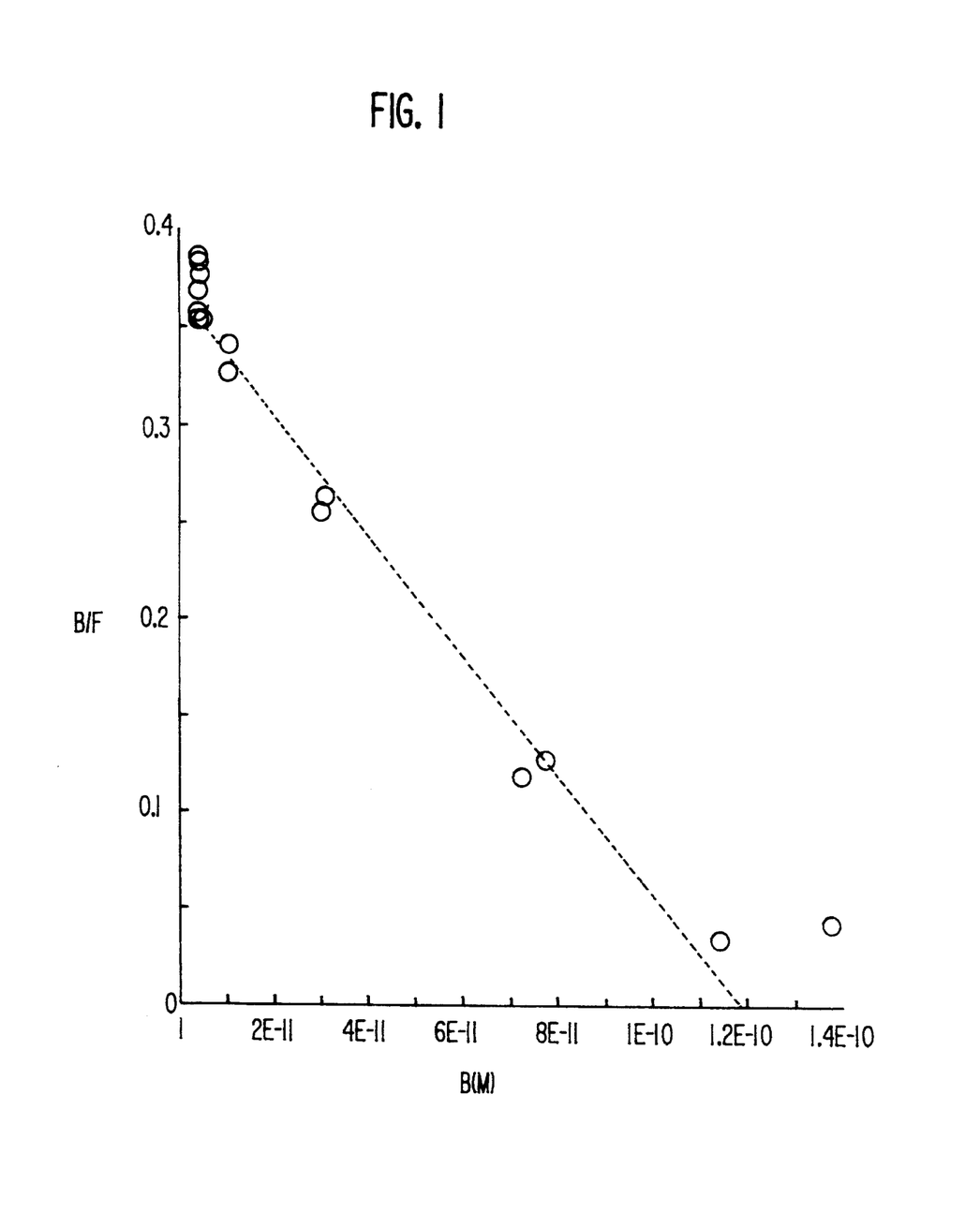
FIG. 1 is a Scatchard plot of an anti-parathyroid hormone-related protein (PTHrP) antibody obtained in Example 1(d).

FIG. 1 is a Scatchard plot of Example 1. Further, the dissociation constant determined in Example 1 is shown below.

Dissociation constant: 0.3 nmol/l (e) Preparation of second antibody solution

From the dissociation constant obtained in the above item, it was determined that the second antibody should be used at a concentration of 1.5 nmol/l. The second antibody was used by diluting it with a phosphate buffered saline containing 2% bovine serum albumin so that its final concentration in the reaction mixture became 1.5 nmol/l concentration.

(f) Preparation of $^{125}$I-labeled anti-rabbit immunoglobulin antibody

According to the method described in W. H. Hunter and F. C. Greenwood, Nature 194, 495 (1962), 0.25 to 40 μg of an anti-rabbit immunoglobulin-goat antibody (produced by Dako Co.) was labeled with 18.5 MBq of $^{125}$I, and the labeled antibody was purified by gel filtration and prepared so as to have a concentration of 4 KBq/0.3 ml by using a phosphate buffered saline containing 4% bovine serum albumin and 0.53% bovine γ-globulin.

(g) Measurement of PTHrP (i) Preparation of calibration curve

A test tube was charged with 0.2 ml of the standard PTHrP solution (0.32 to 1,000 pmol/l), and then 0.1 ml of the second antibody solution and one plastic bead to which the anti-PTHrP monoclonal antibody (first antibody) was bound were charged therein. After the mixture was incubated at room temperature for 20 hours the reaction mixture was removed and the bead was washed with distilled water. Subsequently, 0.3 ml of a solution of the anti-rabbit immunoglobulin-goat antibody labeled with $^{125}$I was added. After incubating the mixture at room temperature for 20 hours the reaction mixture was removed and the bead was washed with distilled water. The radioactivity of the bead was measured by a well-type scintillation gamma counter ARC-1000 (trade name, manufactured by Aloka Co.).

Figure 2:
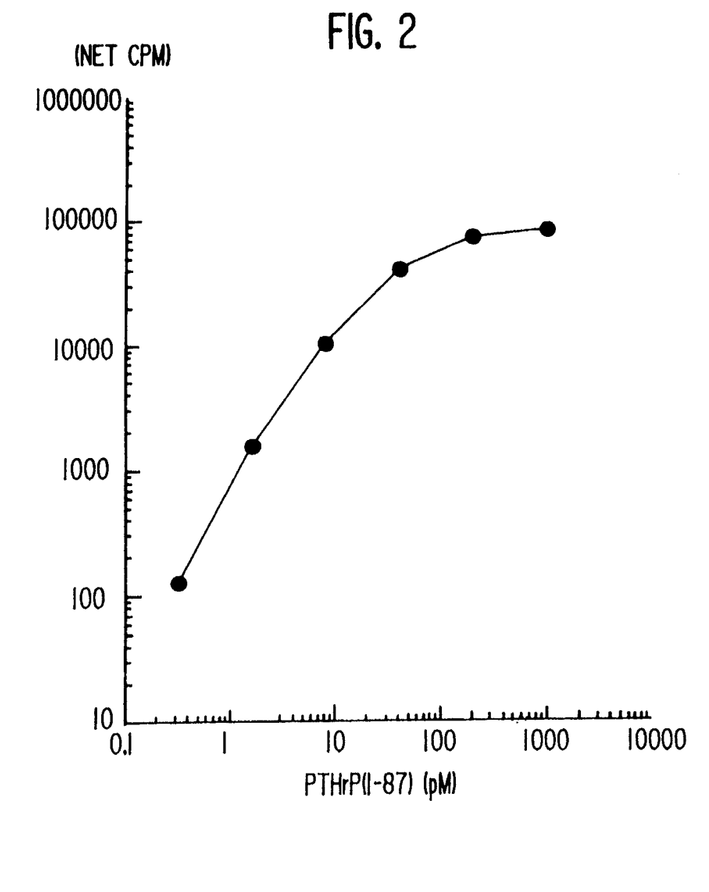
FIG. 2 is a calibration curve of measurement of PTHrP obtained in Example 1.

FIG. 2 is a calibration curve of Example 1. The measurement sensitivity, measurement range and measurement precision (variation coefficient) when the concentration of PTHrP was 8 pmol/l or 200 pmol/l are shown below.

Measurement sensitivity: 0.3 pmol/l
Measurement range: 0.3 to 1,000 pmol/l
Measurement precision: 13% (8 pmol/l) 3% (200 pmol/l)

(ii) Measurement of PTHrP in a sample of humoral hypercalcemia from a malignancy patient PTHrP was measured by the same measurement method described in the above item except for using the serum of a humoral hypercalcemia from a malignancy patient in place of the standard PTHrP as the test sample to be tested. The concentration of PTHrP in the test sample was determined by comparing the calibration curve prepared in the above item with the radioactivity of the test sample. The concentration of PTHrP in the sample to be tested is shown below.

Found value of patient sample: 5.8 pmol/l and 6.0 pmol/l

Comparative Example 1

Measurement of PTHrP (1-87) when the concentration of the second antibody is lower than the dissociation constant between the second antibody and the antigen.

(a) The PTHrP standard solution was prepared according to Example 1(a).
(b) Anti-PTHrP monoclonal antibody (first antibody)-binding plastic beads were prepared according to Example 1(b).
(c) Anti-PTHrP polyclonal antibody (second antibody) was prepared according to Example 1(c).
(d) Second antibody solution was prepared according to Example 1(e).

The second antibody was used by diluting it so that its final concentration in the reaction mixture became 0.0015 nmol/l.

(e) $^{125}$I-labeled anti-rabbit immunoglobulin antibody was prepared according to Example 1(f).
(f) PTHrP was measured according to Example 1(g).

Figure 3:
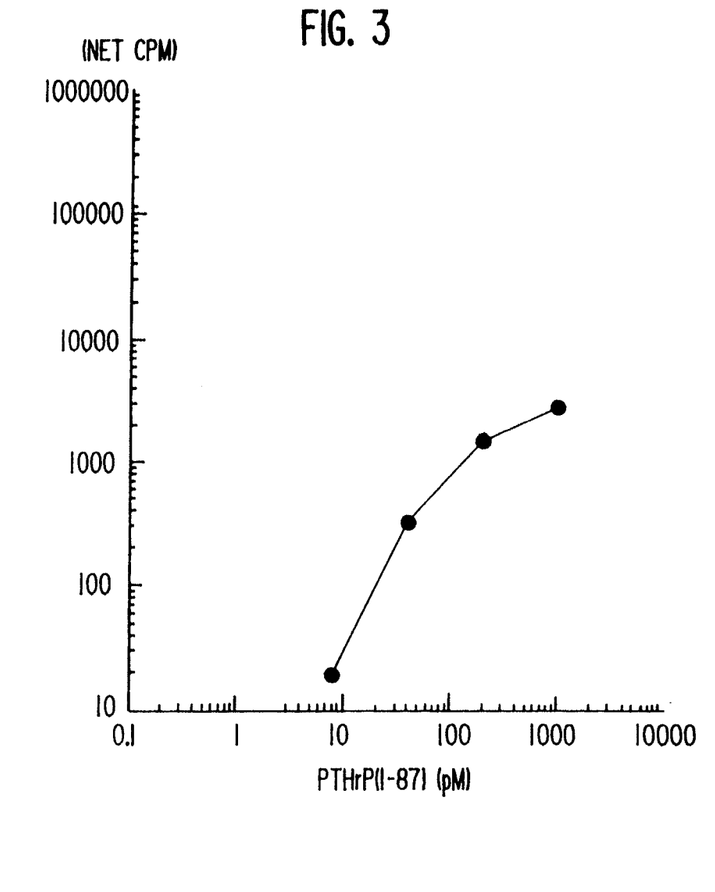
FIG. 3 is a calibration curve of measurement of PTHrP obtained in Comparative example 1.

FIG. 3 is a calibration curve of Comparative Example 1. The measurement sensitivity, measurement range and measurement precision (variation coefficient) when the concentration of PTHrP was 40 pmol/l or 200 pmol/l are shown below.

Measurement sensitivity: 20 pmol/l
Measurement range: 20 to 1,000 pmol/l
Measurement precision: 3.7% (40 pmol/l) 2.8% (200 pmol/l)

Comparative Example 2

Measurement of PTHrP (1-87) according to a conventional sandwich assay method, i.e., in which the second antibody contains a radioactive label.

(a) PTHrP standard solution was prepared according to Example 1(a).
(b) Anti-PTHrP monoclonal antibody (first antibody)-binding plastic beads were prepared according to Example 1(b).
(c) Anti-PTHrP polyclonal antibody (second antibody) was prepared according to Example 1(c).
(d) $^{125}$I-labeled anti-PTHrP polyclonal antibody (labeled second antibody).

The anti-PTHrP polyclonal antibody (second antibody) was labeled and purified according to Example 1(f), and prepared so as to have a concentration of 4 KBq/0.1 ml by using a phosphate buffered saline containing 2% bovine serum albumin.

(e) Measurement of PTHrP

A test tube was charged with the standard PTHrP solution (0.32 to 200 pmol/l) or 0.2 ml of sample serum of a humoral hypercalcemia patient to be tested, and then 0.1 ml of the $^{125}$I-labeled anti-PTHrP polyclonal antibody solution and one plastic bead to which the anti-PTHrP monoclonal antibody was bound were charged therein. After the mixture was incubated at room temperature for 20 hours, the reaction mixture was removed and the bead was washed with distilled water. The radioactivity of the bead was measured by a γ-counter.

Figure 4:
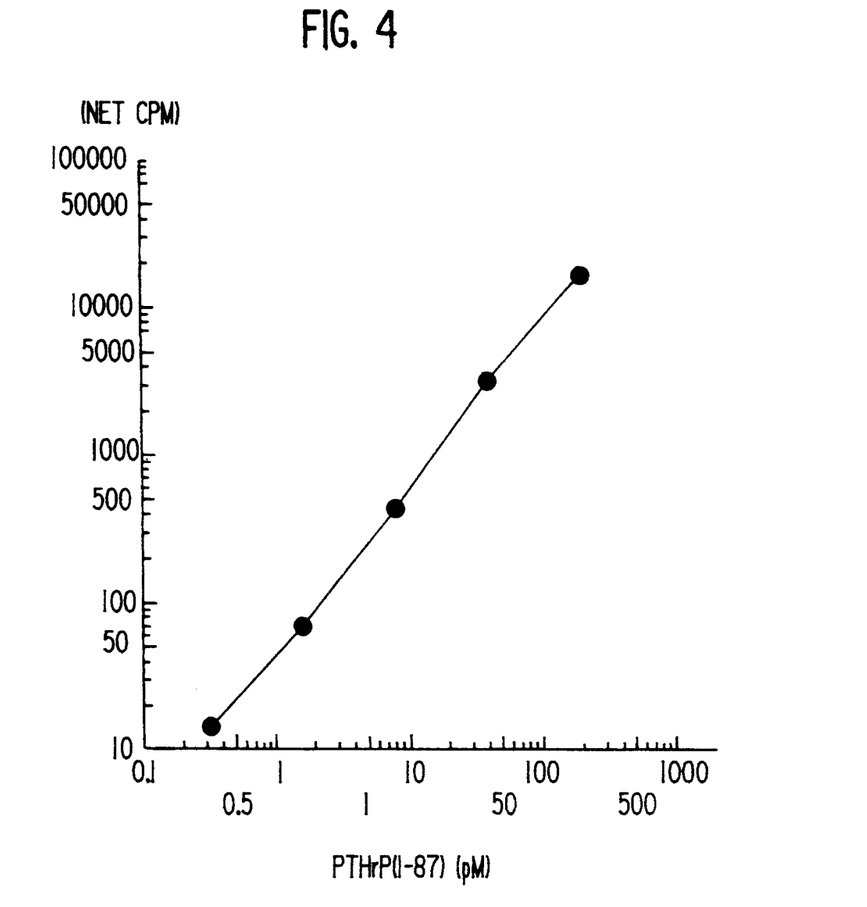
FIG. 4 is a calibration curve of measurement of PTHrP obtained in Comparative example 2.

FIG. 4 is a calibration curve of Comparative example 2. The measurement sensitivity, measurement range, measurement precision (variation coefficient) when the concentration of PTHrP was 40 pmol/l or 200 pmol/l and found values of the patient sample are shown below.

Measurement sensitivity: 20 pmol/l
Measurement range: 20 to 200 pmol/l
Measurement precision: 2.4% (40 pmol/l) 3.4% (200 pmol/l)
Found values of patient sample: all values were lower than measurement sensitivity Example 2

Measurement of adrenocorticotropic hormone (ACTH)

(a) Preparation of ACTH standard solution

After human ACTH obtained from Sigma Co. was hydrolyzed, the solution was prepared so as to have a concentration of 2.2 to 140 pmol/l by using a phosphate buffered saline containing 5% bovine serum albumin and 0.8% bovine γ-globulin based on the quantitated value of concentration by an amino acid analyzer (manufactured by Hitachi Ltd.).

(b) Preparation of anti-ACTH monoclonal antibody (first antibody)-binding plastic beads From spleen cells obtained from mice immunized with ACTH (produced by Sigma Co.) and mouse myeloma cells, a monoclonal hybridoma was obtained according to Example 1(b). Mouse myeloma cells were transplanted to mice, and the ascites were purified to prepare anti-ACTH monoclonal immunoglobulin. The anti-ACTH monoclonal immunoglobulin prepared was coated on plastic beads according to Example 1(b).

(c) Preparation of anti-ACTH polyclonal antibody (second antibody)

According to Example 1(c), rabbits were immunized with ACTH purchased from Sigma Co. to obtain anti-ACTH antiserum. The antiserum was purified to obtain an anti-ACTH polyclonal antibody having high specificity.

(d) The dissociation constant between anti-ACTH polyclonal antibody (second antibody) and ACTH (antigen) was measured according to Example 1(d)

Figure 5:
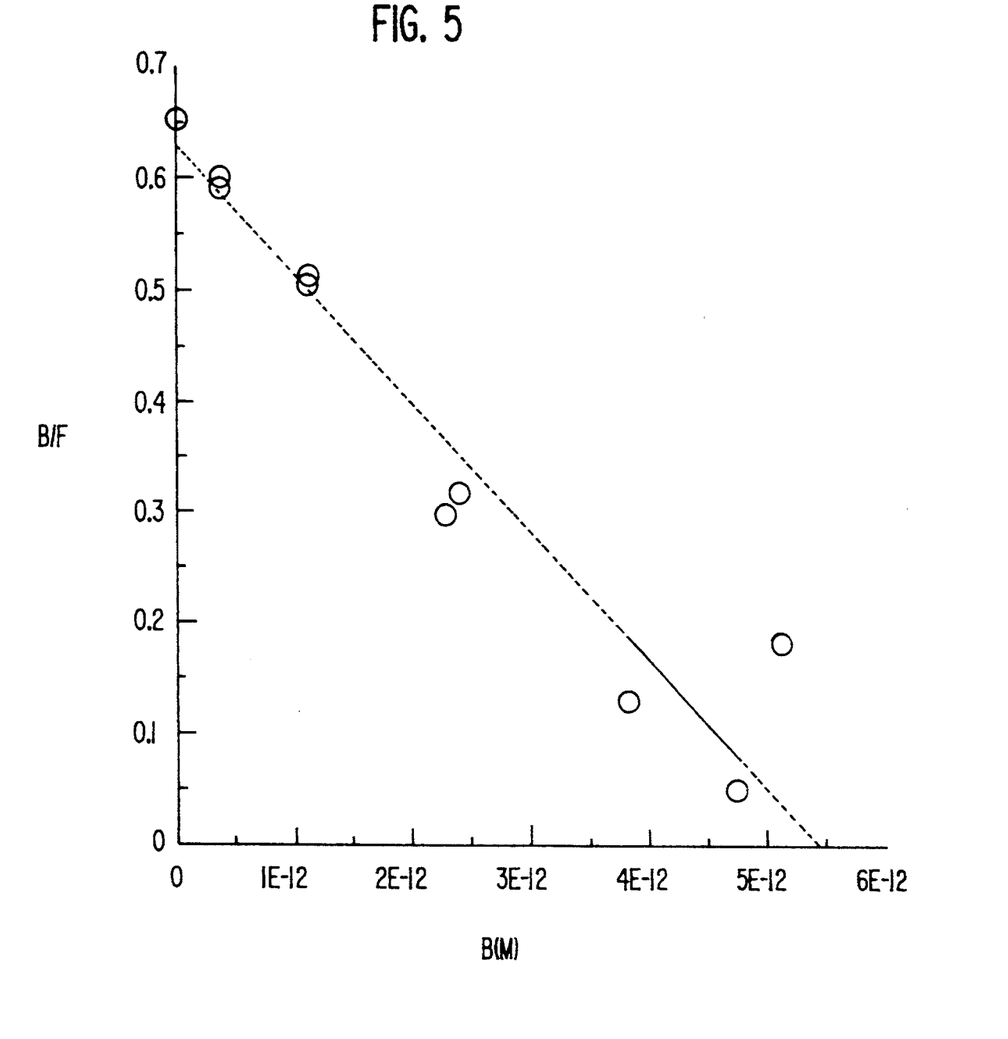
FIG. 5 is a Scatchard plot of an anti-adrenocorticotropic hormone (ACTH) antibody obtained in Example 2(d).

FIG. 5 is a Scatchard plot of Example 2. Further, the dissociation constant determined in Example 2 is shown below.

Dissociation constant: 0.009 nmol/l (e) Preparation of second antibody solution

From the dissociation constant obtained in the above item, it is determined that the second antibody is to be used at a concentration of 0.15 nmol/l. The second antibody was used by diluting it with a phosphate buffered saline containing 2% bovine serum albumin so that its final concentration in a reaction mixture became said concentration.

(f) $^{125}$I-labeled anti-rabbit immunoglobulin antibody was prepared according to Example 1(f)

(g) Measurement of ACTH

A test tube was charged with 0.2 ml of the standard ACTH solution (10 to 640 pg/ml), 0.1 ml of the anti-ACTH polyclonal antibody (second antibody) solution and one plastic bead to which the anti-ACTH monoclonal antibody (first antibody) was bound. After the mixture was incubated at room temperature for 20 hours the reaction mixture was removed and the bead was washed with distilled water. Subsequently, 0.3 ml of a solution of the anti-rabbit immunoglobulin-goat antibody labeled with $^{125}$I was charged. After the mixture was incubated at room temperature for 20 hours the reaction mixture was removed and the bead was washed with distilled water. The radioactivity of the bead was measured by a γ-counter.

Figure 6:
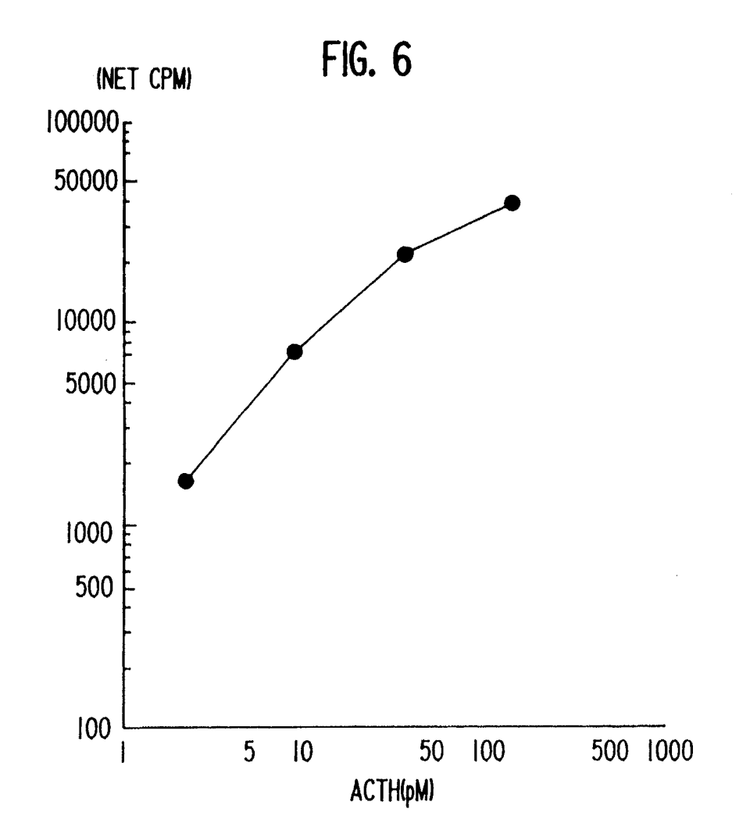
FIG. 6 is a calibration curve of measurement of ACTH obtained in Example 2.

FIG. 6 is a calibration curve of Example 2. The measurement sensitivity, measurement range and measurement precision (variation coefficient) when the concentration of ACTH was 8.9 pmol/l or 140 pmol/l are shown below.

Measurement sensitivity: <2.2 pmol/l
Measurement range: 2.2 to 140 pmol/l
Measurement precision: 10% (8.9 pmol/l) 4.9% (140 pmol/l)

Comparative Example 3

Measurement of ACTH when concentration of the second antibody is lower than the dissociation constant between the second antibody and the antigen.

(a) An ACTH standard solution was prepared according to Example 2(a).
(b) Anti-ACTH monoclonal antibody (first antibody)-binding plastic beads were prepared according to Example 2(b).
(c) Anti-ACTH polyclonal antibody (second antibody) was prepared according to Example 2(c).
(d) The second antibody solution was prepared according to Example 2(e).

The second antibody was used by diluting it so that its final concentration in the reaction mixture became 0.0015 nM.

(e) $^{125}$I-labeled anti-rabbit immunoglobulin antibody was prepared according to Example 1(f).
(f) ACTH was measured according to Example 2(g).

Figure 7:
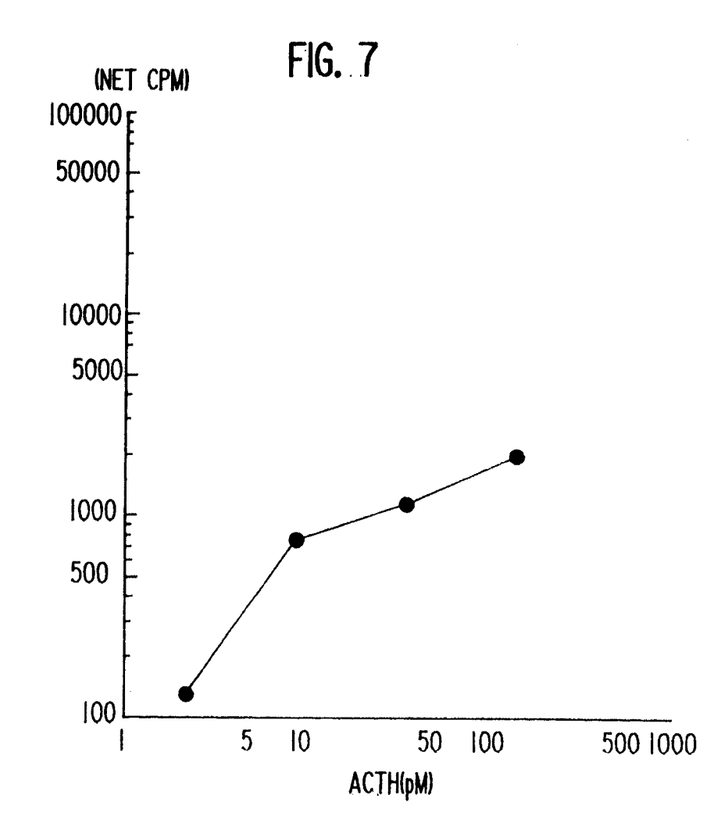
FIG. 7 is a calibration curve of measurement of ACTH obtained in Comparative example 3.

FIG. 7 is a calibration curve of Comparative Example 3. The measurement sensitivity, measurement range and measurement precision (variation coefficient) when the concentration of ACTH was 36 pmol/l or 140 pmol/l are shown below.

Measurement sensitivity: 25 pmol/l
Measurement range: 25 to 140 pmol/l
Measurement precision: 13% (36 pmol/l) 3.4% (140 pmol/l)

Comparative Example 4

Measurement of ACTH according to a conventional sandwich assay method, i.e., in which the second antibody contains a radioactive label.

(a) An ACTH standard solution was prepared according to Example 2(a).

(b) Anti-ACTH monoclonal antibody (first antibody)-binding plastic beads were prepared according to Example 2(b).

(c) Anti-ACTH polyclonal antibody (second antibody) was prepared according to Example 2(c).

(d) Preparation of $^{125}$I-labeled anti-ACTH polyclonal antibody (labeled second antibody).

The anti-ACTH polyclonal antibody (second antibody) was labeled and purified according to Example 1(f), and prepared so as to have a concentration of 4 KBq/0.1 ml by using a phosphate buffered saline containing 2% bovine serum albumin.

(e) Measurement of ACTH

A test tube was charged with 0.2 ml of the standard ACTH solution (2.2 to 140 pmol/l), and then 0.1 ml of the $^{125}$I-labeled anti-ACTH polyclonal antibody solution and one plastic bead to which the anti-ACTH monoclonal antibody was bound were charged therein. After the mixture was incubated at room temperature for 20 hours the reaction mixture was removed and the bead was washed with distilled water. The radioactivity of the bead was measured by a counter.

Figure 8:
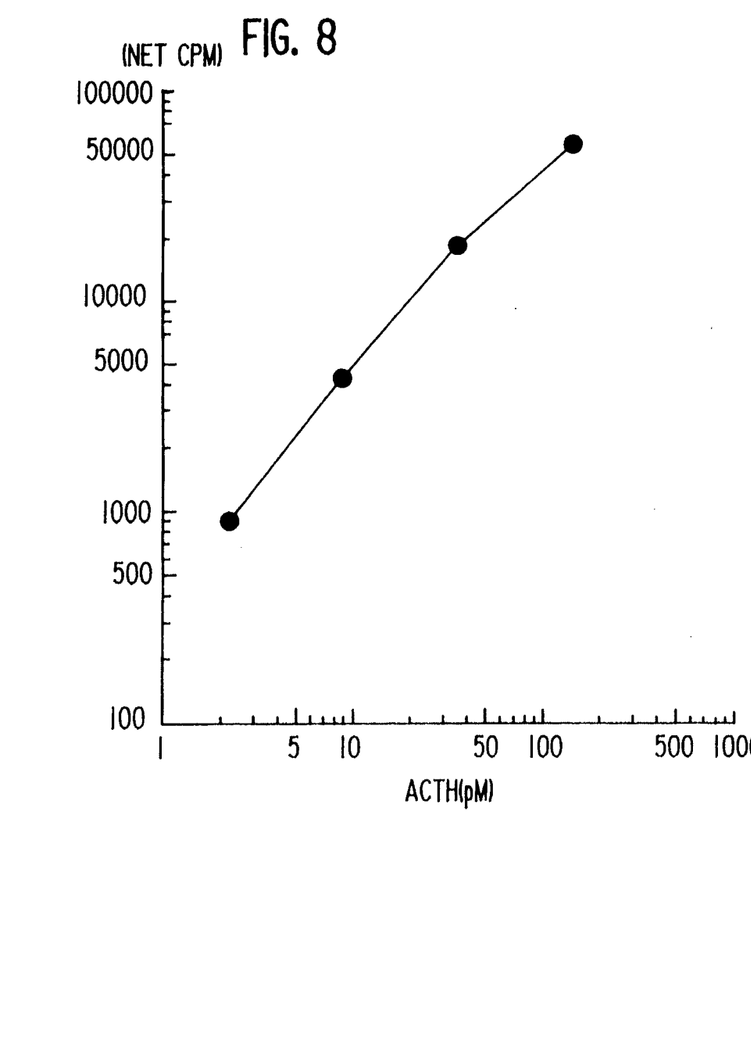
FIG. 8 is a calibration curve of measurement of ACTH obtained in Comparative example 4.

FIG. 8 is a calibration curve of Comparative Example 4. The measurement sensitivity, measurement range and measurement precision (variation coefficient) when the concentration of ACTH was 8.9 pmol/l or 140 pmol/l are shown below.

Measurement sensitivity: 2.5 pmol/l
Measurement range: 2.5 to 140 pmol/l
Measurement precision: 5.7% (8.9 pmol/l) 2.4% (2 to 4 pmol/l)

Example 3

Measurement of endothelin (ET)

(a) Preparation of ET standard solution

Human endothelin (ET) obtained from Peptide Institute Co., Japan was prepared so as to have a concentration of 5 to 500 pg/ml by using a phosphate buffered saline containing 5% bovine serum albumin and 0.8% bovine γ-globulin.

(b) Preparation of anti-ET monoclonal antibody (first antibody)-binding plastic beads.

Anti-ET monoclonal immunoglobulin prepared according to Example 1(b) was coated on plastic beads.

(c) Preparation of anti-ET polyclonal antibody (second antibody)

ET antiserum obtained by immunizing rabbits with ET was purified to obtain an anti-ET polyclonal antibody having high specificity according to Example 1(c).

(d) The dissociation constant between anti-ET polyclonal antibody (second antibody) and ET (antigen) was measured according to Example 1(d). The dissociation constant determined in Example 3 is shown below.

Dissociation constant: 0.08 nmol/l (e) Preparation of second antibody solution.

From the dissociation constant obtained in the above item, it is determined that the second antibody should be used in a concentration of 0.6 nmol/l. The second antibody was used by diluting it with a phosphate buffered saline containing 2% bovine serum albumin so that its final concentration in the reaction mixture became said concentration.

(f) $^{125}$I-labeled anti-rabbit immunoglobulin antibody was prepared according to Example 1(f).

(g) Measurement of ET

A test tube was charged with 0.2 ml of the standard ET solution (5 to 500 pg/ml), 0.1 ml of the anti-ET polyclonal antibody solution and one plastic bead to which the anti-ET monoclonal antibody was bound. After the mixture was incubated at room temperature for 20 hours, the reaction mixture was removed and the bead was washed with distilled water. Subsequently, 0.3 ml of a solution of the anti-rabbit immunoglobulin-goat antibody labeled with $^{125}$I was charged. After the mixture was incubated at room temperature for 20 hours, the reaction mixture was removed and the bead was washed with distilled water. The radioactivity of the bead was measured by a γ-counter.

Figure 9:
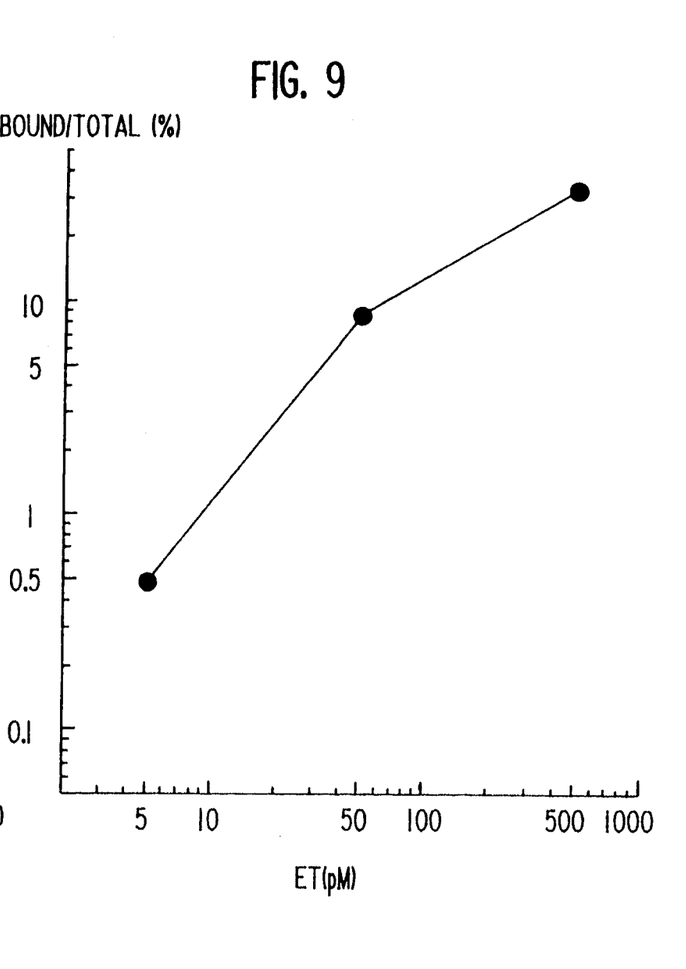
FIG. 9 is a calibration curve of measurement of endotherine (ET) obtained in Example 3.

FIG. 9 is a calibration curve of Example 3. The measurement sensitivity and measurement range are shown below.

Measurement sensitivity: <5 ng/ml
Measurement range: to 500 ng/ml

Comparative Example 5

Measurement of ET according to a conventional sandwich assay method in which second antibody is labeled directly.

(a) An ET standard solution was prepared according to Example 3(a).

(b) Anti-ET monoclonal antibody (first antibody)-binding plastic beads were prepared according to Example 3(b).

(c) Anti-ET polyclonal antibody (second antibody) was prepared according to Example 3(c).

(d) Preparation of $^{125}$I-labeled anti-ET polyclonal antibody (labeled second antibody)

The anti-ET polyclonal antibody (second antibody) was labeled and purified according to Example 1(f), and prepared so as to have a concentration of 4 KBq/0.1 ml by using a phosphate buffered saline containing 2% bovine serum albumin.

(e) Measurement of ET

In a test tube was charged 0.2 ml of the standard ET solution (5 to 500 pmol/l), and then 0.1 ml of the $^{125}$I-labeled anti-ET polyclonal antibody solution and one plastic bead to which the anti-ET monoclonal antibody was bound were charged therein. After the mixture was incubated at room temperature for 20 hours the reaction mixture was removed and the bead was washed with distilled water. The radioactivity of the bead was measured by a γ-counter.

Figure 10:
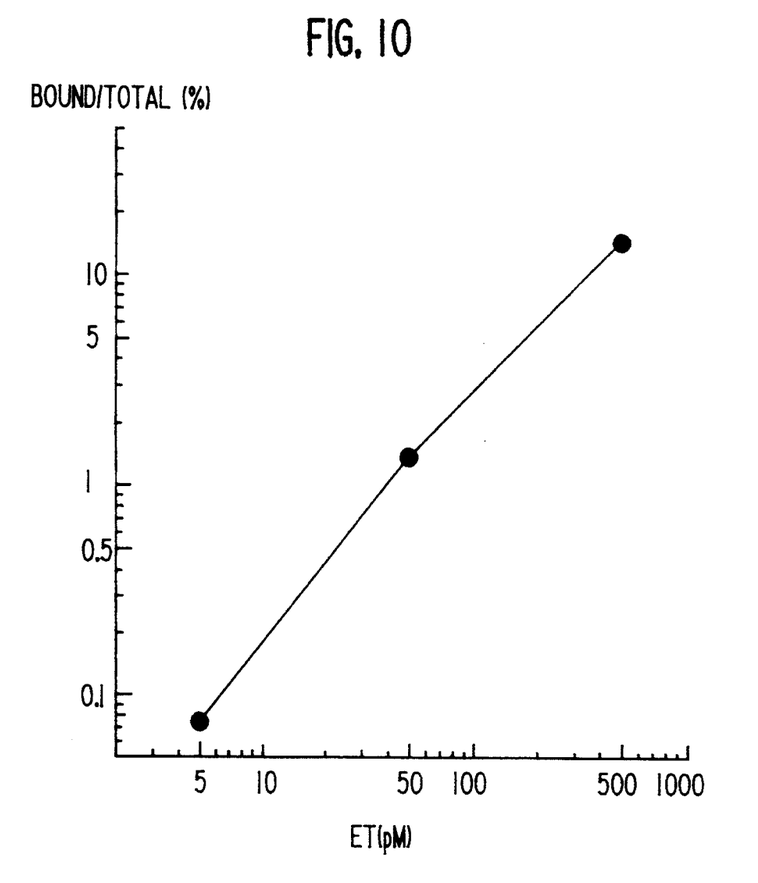
FIG. 10 is a calibration curve of measurement of ET obtained in Comparative example 5.

FIG. 10 is a calibration curve of Comparative Example 5. The measurement sensitivity and measurement range are shown below.

Measurement sensitivity: 25 pmol/l
Measurement range: 25 to 500 pmol/l

Example 4

Measurement of atrial natriuretic peptide (ANP)

In order to examine relation between measurement sensitivity and the dissociation constant between a second antibody and an antigen, ANP was measured by using various concentrations of a second antibody.

(a) Preparation of ANP standard solution

Human ANP obtained from Peptide Institute Co., Japan was prepared so as to have a concentration of 50 pg/ml by using a phosphate buffer solution containing 0.1% bovine serum albumin.

(b) Preparation of anti-ANP monoclonal antibody (first antibody)-binding plastic beads.

Anti-ANP monoclonal immunoglobulin prepared according to Example 1(b) was coated on plastic beads.

(c) Preparation of anti-ANP polyclonal antibody (second antibody).

Anti-ANP antiserum obtained by immunizing rabbits with ANP was purified to obtain an anti-ANP polyclonal antibody having high specificity.

(d) The dissociation constant between anti-ANP polyclonal antibody (second antibody) and ANP (antigen) was measured according to Example 1(d).

The dissociation constant determined in Example 4 is shown below.

Dissociation constant: 0.078 nmol/l (e) Preparation of second antibody solution

From the dissociation constant obtained in the above item, it is determined that the second antibody is to be used at a concentration of 0.0015 to 15 nmol/l. The second antibody was used by diluting it with a phosphate buffer solution containing 0.1% bovine serum albumin so that its final concentration in a reaction mixture became said concentration.

(f) $^{125}$I-labeled anti-rabbit immunoglobulin antibody was prepared according to Example 1(f).

(g) Measurement of ANP

In a test tube were charged 0.2 ml of the standard ANP solution (50 pg/ml), 0.1 ml of the anti-ANP polyclonal antibody solution (final concentration: 0.0015 to 15 nmol/l) and one plastic bead to which the anti-ANP monoclonal antibody was bound. After the mixture was incubated at room temperature for 20 hours the reaction mixture was removed and the bead was washed with distilled water. Subsequently, 0.3 ml of a solution of the anti-rabbit immunoglobulin-goat antibody labeled with $^{125}$I was charged. After the mixture was incubated at room temperature for 20 hours, the reaction mixture was removed and the bead was washed with distilled water. The radioactivity of the bead was measured by a γ-counter.

Figure 11:
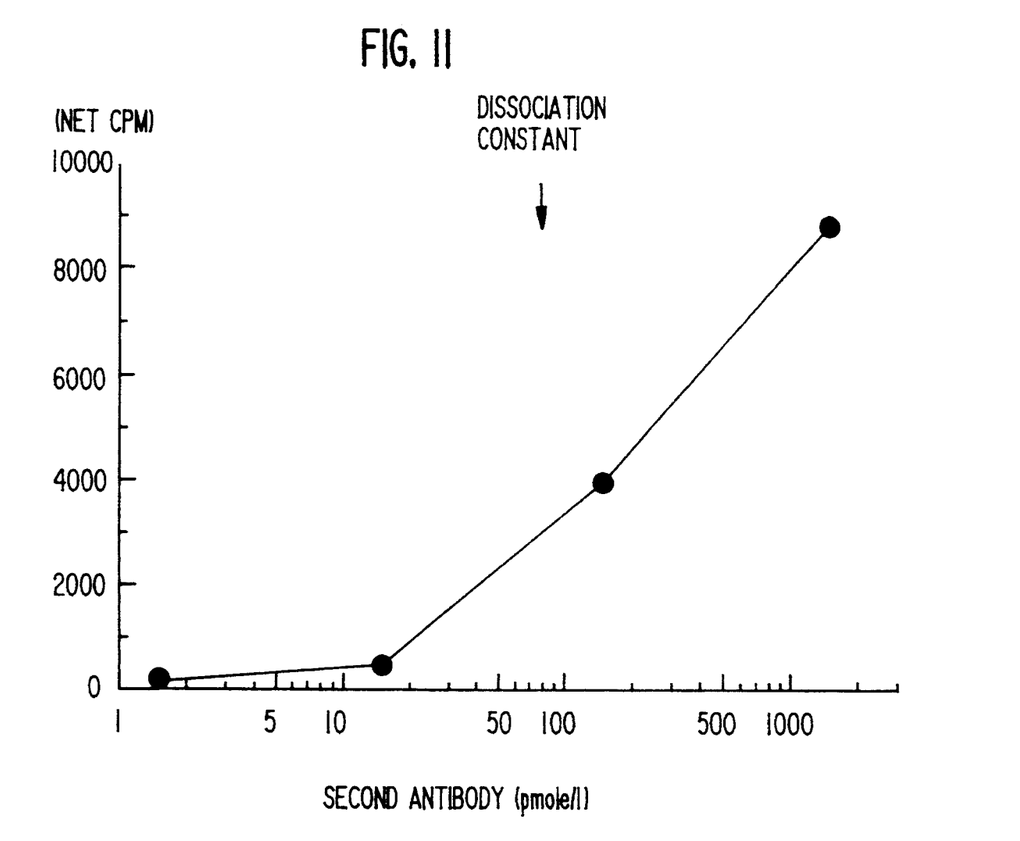
FIG. 11 is a dose response curve of a second antibody in a measurement system of atrial natriuretic peptide (ANP) obtained in Example 4.

FIG. 11 is a dose response curve of Example 4. From the point where the concentration of the second antibody exceeds the dissociation constant between the second antibody and the antigen, the radioactivity of the bead is elevated remarkably.

By comparing Example 1 with Comparative Example 1 and Example 2 with Comparative Example 3, respectively, it is apparent that in the assay of the present invention, sensitivity increased remarkably by reacting the second antibody at a concentration higher than the dissociation constant between the second antibody and the antigen, as compared with the case where the second antibody is reacted at a concentration lower than said dissociation constant. Further, even when compared with the conventional sandwich assay method, in which a second antibody is labeled directly, (Comparative Examples 2, 4 and 5) improvements in measurement sensitivity are observed in all Examples of the present invention. When a second antibody having only low sensitivity is available (i.e., having a large dissociation constant) as in the cases of PTHrP and ET, the effect is particularly remarkable. When a second antibody having relatively high sensitivity (Kd=$9 \times 10^{-12}$ mol/l) is available, as in the case of ACTH, improvement of measurement sensitivity is also observed. Thus, when the sensitivity (dissociation constant between a second antibody and an antigen) of the second antibody is at least larger than $9 \times 10^{-12}$ mol/l, the assay of the present invention can exhibit its effect to particular advantage.

In Example 4, the radioactivity of the bead is elevated remarkably from the point where the concentration of the second antibody exceeds the dissociation constant between the second antibody and the antigen. Thus, it is important to use a second antibody at a concentration higher than the dissociation constant. The present assay provides a measurement system with high sensitivity which can be constituted without the absolute requirement of obtaining a second antibody having high sensitivity.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A radioimmunoassay method comprising the steps:
   (i) reacting a first antibody (A) which is specific for an antigen (B) and immobilized on an insoluble solid; an antigen (B); and a second antibody (C) which is derived from a different animal species than that of antibody (A); wherein the concentration of the second antibody (C) is higher than the dissociation constant between the second antibody (C) and the antigen (B), to obtain an immune complex (D);
   (ii) reacting the immune complex (D) and a radiolabeled probe (E) specific for the second antibody (C); and
   (iii) measuring the radioactivity of the insoluble solid or the reaction mixture obtained in step (ii) and determining the amount of antigen (B).

2. The assay of claim 1, wherein the antigen (B) is an antigenic substance selected from the group consisting of a peptide hormone, a steroid hormone, thyroxine, triiodothyronine, a serum protein, a carcinoma-related antigen, an antigenic component of a bacterium, an antigenic component of a virus and an antigenic component of a protozoan.

3. The assay of claim 2, wherein the peptide hormone is parathyroid hormone-related protein (PTHrP).

4. The assay of claim 2, wherein the peptide hormone is adrenocorticotropic hormone (ACTH).

5. The assay of claim 2, wherein the peptide hormone is endothelin (ET).

6. The assay of claim 1, wherein the antigen (B) is atrial natriuretic peptide (ANP).

7. The assay of claim 1, wherein the first antibody (A) is a polyclonal antibody.

8. The assay of claim 1, wherein the first antibody (A) is a monoclonal antibody.

9. The assay of claim 1, wherein the insoluble solid is selected from the group consisting of glass, silica gel, bentonite, a magnetic material, a plastic, a polymer gel and a filter.

10. The assay of claim 1, wherein the second antibody (C) is a polyclonal antibody.

11. The assay of claim 1, wherein the first antibody (A) is a monoclonal antibody and the second antibody (C) is a polyclonal antibody.

12. The assay of claim 1, wherein the first antibody (A) on the insoluble solid is a biotylated first antibody which is immobilized on solid phase-bound avidin.

13. The assay of claim 1, wherein the probe (E) is an antibody which identifies immunoglobulin derived from the same species of animal as that of the second antibody (C).

14. The assay of claim 1, wherein the second antibody (C) is bound to biotin.

15. The assay according to claim 14, wherein the probe (E) is selected from the group consisting of avidin and streptavidin.

16. The assay of claim 1, wherein the dissociation constant between the second antibody (C) and the antigen (B) is in the range of $10^{-6}$ to $9 \times 10^{-12}$ mol/l.

17. The assay of claim 16, wherein the dissociation constant between the second antibody (C) and the antigen (B) is in the range of $10^{-8}$ to $10^{-11}$ mol/l.

18. The assay of claim 1, wherein the radioisotope is Iodine 125.

19. The assay of claim 1, wherein the concentration of the second antibody (C) is more than 1.0 and up to 10 times the dissociation constant between the second antibody (C) and the antigen (B).

* * * * *